United States Patent [19]

Harendza-Harinxma

[11] Patent Number: 4,672,074

[45] Date of Patent: Jun. 9, 1987

[54] OINTMENT AND PROCESS FOR TREATING SKIN LESIONS

[76] Inventor: Alfred J. Harendza-Harinxma, 50 Merion Pl., Lawrenceville, N.J. 08648

[21] Appl. No.: 691,832

[22] Filed: Jan. 16, 1985

Related U.S. Application Data

[63] Continuation-in-part of Ser. No. 456,542, Jan. 10, 1983, abandoned.

[51] Int. Cl.$^4$ ............................................. A61K 31/40
[52] U.S. Cl. .................................. 514/420; 514/415; 514/887
[58] Field of Search ................................ 514/415, 420

[56] References Cited

U.S. PATENT DOCUMENTS 3,838,167  9/1974  Jones .............................. 260/326.16
4,263,313  4/1981  Eckert et al. ..................... 424/273 P
4,309,414  1/1982  Iragi et al. ............................ 424/81

OTHER PUBLICATIONS

Inglot et al, Arch. Immunol. Ther. Exp; 1971 19(4) 555–66.
Chemical Abstracts 74:57306m.
Chemical Abstracts 85:99193e (1976).
Merck Index—9th ed, 1976; p. 656, 914840.

Primary Examiner—Leonard Schenkman
Attorney, Agent, or Firm—Alan M. Sack; Richard C. Woodbridge

[57] ABSTRACT

An ointment containing Indole or an Indole derivative such as Indomethacin and a base; and a process for treating inflammations and lesions on the human skin including the step of applying an ointment containing such an ingredient to the sore.

7 Claims, No Drawings

OINTMENT AND PROCESS FOR TREATING SKIN LESIONS

PRIOR APPLICATION

This application is a continuation-in-part of a parent application by the same inventor having the Ser. No. 456,542, filed Jan. 10, 1983 abandoned.

BACKGROUND OF THE INVENTION

1. Field of the Invention

This invention relates to salves and solutions. It further relates to salves, lotions, jellies and solutions (compositions) for treatment of inflamed areas of skin, including areas exhibiting lesions.

It further relates to compositions for treatment of such inflamed skin areas where the inflamation is caused by a virus.

It further relates to compositions for treatment of inflamed skin where the inflammation is caused by any variety of Herpes virus, including Herpes Zoster, Herper Simplex I, and Herpes Simplex 2.

2. Description of the Prior Art

The Physician's Desk Reference (PDR) has 34 categories of dermatological preparations, including antibacterial and antifungal. However, there is no "antiviral" heading. The three anti-inflammatory agents listed all utilize a corticosteroid as their active ingredient. However, they do not heal the inflammations or lesions produced by the Herpes viruses.

None of the listed salves, ointments, foams, lotions or other materials intended for topical use employ Indole or derivatives of Indole such as Indomethacin, Tryptophan, Indole-3-propionic acid, Indole-3-acetic acid, Indole-3-carboxylic acid or Tryptophol. Mercks Manual of Diagnosis and Therapy suggests for Herpes Simplex topical use of Idoxuridine (IDU) for herpetic keratitis (eye infection), but this material is not found in PDR. Mercks mentions Acyclovir as having shown promise in the treatment of Herpes lesions.

For other Herpes lesions, Mercks suggests 'drying lotions' such as Camphor Spirit or 70% alcohol. For Herpes Zoster, Merck states "there is no known specific therapy."

Proteolytic enzymes which attack and degrade proteins, while claimed to have anti-inflammatory effects have no effect on Herpes inflammations or lesions.

Hormones which directly or indirectly cause the adrenal cortex to produce and secrete steroids, represent another class of anti-inflammatory compounds. However, no known hormones have produced a satisfactory response in the treatment of Herpes inflammation or lesions.

Inglot (TOPICAL TREATMENT OF CUTANEOUS HERPES SIMPLEX IN HUMANS WITH THE NON-STEROID ANTIINFLAMMATORY DRUGS: MEFENAMIC ACID AND INDOMETHACIN IN DIMETHYLSULFOXIDE Arichivum Immunologiae et Therapiae Experimentalis, 19, 555, 1971) used Indomethacin, an Indole-containing compound and Mefenamic acid a non-Indole containing compound in a highly toxic carrier, dimethylsulfoxide (DMSO) to heal Herpes sores. Inglot chose the carrier DMSO because it was a vehicle which " . . . facilitates their penetration into the skin." Inglot states that she did not test the DMSO carrier alone on Herpes sores.

Eckert (U.S. Pat. No. 4,263,313 issued Apr. 21, 1981) discloses a carrier for Indomethacin to be applied to the skin of rheumatically affected people. The expressed objective of the carrier is to improve the absorption of the active compound into the skin. Eckert's objective is to get Indomethacin into the body without traversing the intestinal tract, not to treat a disease of the skin.

Silber (U.S. Pat. No. 3,629,412 issued Dec. 21, 1971) teaches Indomethacin as a topical ingredient with methylsalicyclate (oil of wintergreen). Silber's primary objective, like Eckert is to get Indomethacin into the body without traversing the alimentary tract, though he suggests topical effectiveness on skin inflammations generally.

At present no antiviral agents in a non-toxic base, free from side-effects and effective in the neutralization of pain and the inflammatory response caused by the Herpes virus are known.

Indomethacin

Indomethcin is a synthetic, non-steroidal compound also containing the Indole structure. This differentiates it from compounds such as salisylates, corticosteroids, phenylbutazone-like compounds and colchicine. Indomethacin is more or less soluble in ethyl alcohol, chloroform, ether, and acetone. It is substantially insoluble in cold water and cod liver oil. PDR lists Indomethacin as a drug for oral use. There is no discussion or suggestion of topical use for any purpose. Indomethacin and other Indole derivatives were patented on Dec. 15, 1964 by Shen Pat. No. 3,161,654, now expired. The Patent sets forth procedures for producing the material. The Merck Index describes Indomethacin as an anti-inflammatory, anti-pyretic, analgesic agent. Indomethacin is well known to physicians under the Merck tradename of Indocin. Merck supplies the drug in pill form only containing 25, 50 and 75 milligrams of the active ingredient.

The Modern Drug Encyclopedia edited by Arthur J. Lewis, MD states that Indomethacin " . . . is orally administered for rheumatoid arthritis, rheumatoid (anklosing), spondylitis, degenerative joint diseases (osteoarthritis) of the hips, knees and shoulders, and for gout. During the interval phase of gouty arthritis, Indomethacin together with adequate doses of a uricosuric agent may relieve pain and prevent the recurrance of acute attacks.

"The adverse reactions of Indomethacin on humans may include headache, dizziness, lightheadedness, syncope, drowsiness, convulsions, peripheral neuropathy, diarrhea, single or multiple ulcerations, bleeding in gastrointestinal tract without obvious ulcer, elevated blood pressure, angiitis, skin rashes, and acute respiratory distress including sudden dyspnea and asthma."

BRIEF SUMMARY OF THE INVENTION

This invention is directed toward a composition for topical use in treatment of skin disease typically caused by a virus of the Herpes type. The active ingredients of the compositions are Indole and derivatives of Indole such as Indomethacin, Tryptophan, Indole-2-carboxylic acid, Indole-3-propionic acid, Indole-3-acetic acid and Tryptophol when used in a base such as petrolatum or Desitin brand ointment which limits the absorption of the active ingredient through the skin, thereby maintaining a high concentration of the active ingredient in close contact with the affected area and limiting side effects. Desitin ® is a registered trademark of the Leeming Division of Pfizer Inc., 325 E. 42nd Street, New York, NY 10017 for an over-the-counter salve to sooth babies skin.

DETAILED DESCRIPTION OF THE DISEASE

Herpes, the Illness and its Treatment

Herpes is spreading in the United States at an alarming rate. It is estimated that between 20 and 35 million Americans already have the disease and another half million are expected to contract it each year.

The first symptoms of Herpes infections are commonly a sensitivity or inflammation consisting of a burning sensation, tingling, itching and/or a minor rash on the skin. As used herein, the term skin includes oral, genital and anal mucosa. Some individuals also note pains in the lower back and legs. These symptoms are known as the prodrome. Within a few hours to up to two days, a few red marks will appear on the involved area. After a few more areas those marks become raised and full of fluid, looking much like blisters on a red base. The blisters are small, usually only 2–5 mm wide, and are often clustered. The blisters rupture, emitting an exudate, and the ulcers are usually very painfull. The individual may also experience low fever, malaise, muscular aches, vaginal burning and/or discharge in a woman, pain and itching of the penis in a main, frequent urination, and swelling of the thigh and neck/lymph glands. This last group of symptoms is more pronounced if it is an individual's first outbreak of Herpes. The lesions associated with the initial outbreak often last 2–6 weeks.

Between 50 and 67% of Herpes victims experience recurrence of the sores. This can happen any time; days, months or even years after the initial outbreak. It is thought that the virus lodges in nerve cells until it is triggered to renewed activity by some type of stress—emotional, menstrual, dietary or physical—that varies from person to person. Recurrences tend to be confined to one area, are less intense, and are shorter (about 8–14 days). Symptoms and sores are similar to those experienced during the primary infection, though often less severe.

Although Herpes sores in most cases are merely unsightly and acutely uncomfortable, the exudate poses a severe transmission problem when brought in contact with the mucus membranes (mouth, genitalia, eyes) of another person, or the patient himself.

In one case, Herpes lesions can be life threatening; a newborn infant, born of a mother exhibiting genital Herpes lesions, stands a high probability of contracting the disease. Herpes in the newborn can result in death or brain damage.

Therefore, a treatment which prevents the formation of or promotes the healing of Herpes lesions not only heals the patient but also reduces the transmissibility of the disease to the patient and to others.

The Medical Dictionary edited by Dorland defines an inflammation as "a localized protective response elicited by injury or destruction of tissues which serves to destroy, dilute or wall off both the injurious agent and the injured tissue. It is characterized in the acute form by the classical sequence of pain, heat, redness, swelling and the loss of function. Histologically, it involves a complex series of events including dilation of the aterioles, capillaries and venules with increased permeability and blood flow, exudation of fluids, increasing plasma protenis, and leukocytic migration into inflammatory focus."

The inflammatory response is any response characterized by inflammation as described above. Inflammation of the tissues may be caused by bacteria or viruses or by mechanical, chemical or irradiation irritation. This specification restricts discussion to inflammatory responses caused by viruses; however the discussion is also valid when applied to inflammatory responses caused by bacteria.

Viruses

At present, we know that a number of different viruses possess the property of infectivity, and that they differ from bacteria in that they lack a cell wall and the related enzymes systems. Viruses are classified on the basis of either Deoxyribonucleic acid (DNA) or Ribonucleic acid (RNA). In most cases the known antiviral agents that affect DNA virus replication have no effect on RNA viruses, and vice-versa. Many strains of the viruses exist, and the differences between them are detected on the basis of immunological responses.

DNA viruses include the following:
a. Poxviruses (e.g. vaccinia, variola, myxoma)
b. Herpes Viruses. There are a number of known Herpes viruses, though there may be still more Herpes viruses to be found. TABLE 1 provides a brief summary of the known viruses:

TABLE 1

| NAME OF VIRUS | MEDICAL NAME OF DISEASE | COMMON NAME OF DISEASE |
|---|---|---|
| Herpes Simplex I | Varicella Herpes Simplex | Chickenpox Fever Blisters |
| Herpes Simplex 2 (HSV-2) | Herpes Genitalis | Genital Herpes |
| Varicella Zoster (VZ) Zoster | Herpes Zoster | Shingles |
| | VZ (Zoster) may cause Chickenpox in non-immune children and Shingles in partially immune adults. | |
| Epstein Barr (ESBV) EB Herpes virus | Infectious Mononucleosis | Mononuleosis (Mono) |
| Cytomegalo | Jaundice Hepatosplenomegaly | Jaundice | c. Adenoviruses. Many types of these are known. This type is believed to be responsible for acute respiratory diseases.
d. Papoviruses such as papilloma, polyome and SV 40 in Rhesus monkeys.

RNA Viruses include the following:
a. Myxoviruses. These cause influenza A B and C, mumps, swine influenza and fowl plague.
b. Arboviruses. These cause equine encephalomyelitis, Sindbis, yellow fever and Semliki Forest.
c. Picornaviruses. These cause Polio, Coxsackie, and enteric cytopathogenic human orphans (ECHO)
d. Rhinoviruses. These are a subgroup of Picornaviruses associated with the common cold of man.

The Tests

The present invention is related to compounds which will safely and effectively treat the Herpes symptoms of inflammation and lesions when applied to skin affected by Herpes inflammations or lesions. The following materials were used in a wide variety of concentrations ranging from pure compound to 0.1%. In all cases where a carrier or base was used a non-toxic material was employed which was believed would have the dual functions of: a. delaying absorption through the skin to maintain the highest concentration of the compound on the surface of the diseased skin and b. by delaying absorption through the skin to minimize possible side effects such as those which have been documented for Indomethacin in this application under the PRIOR ART heading.

a. acetylsalicyclic acid (aspirin)
b. 4-Butyl-1,2-diphenyl-3,5-pyrazolidinedione (Phenylbutazone)
c. 2-[(2,3-dimethylphenyl)amino]-benzoic acid (Mefenamic acid)
d. alpha( )-methyl-4-(2-methylpropyl)-benzene-acetic acid (Ibuprofen)
e. 1-(4-chlorobenzoyl)-5-methoxy-2-methyl-1H-indole-3-acetic acid; or 1-(p-chlorobenzoyl)-5-methoxy-2-methylindole-3-acetic acid (Indomethacin)
f. Indole-3-ethanol (Tryptophol)
g. Indole-2-carboxylic acid
h. Indole-3-propionic acid
i. Indole-3-acetic acid
j. L-alpha-amino-3-indole propionic acid (L-Tryptophan)
k. Indole It was found that aspirin, phenylbutazone, mefanamic acid and Ibuprofen, also known as Motrin, were ineffective in the in-vivo topical treatment of Herpes inflammations or sores.

However, it was found that all the compounds containing an Indole group and Indole itself were effective, though not uniformly effective, in controlling pain and rapidly healing lesions and suppressing inflammations caused by Herpes viruses, and the lesions and inflammations believed to be caused by other DNA viruses.

The active compound, if solid, should be ground to pass 200 mesh. The following salves are typical of those which can be formulated using the nontoxic bases disclosed.

Salves

Salve Formulation No. 1

30 grams Indomethacin (3%)
970 Desitin ® brand ointment

In place of Desitin ® the following mixture can be used.

| | |
|---|---|
| 400 grams | Zinc Oxide |
| 140 grams | petrolatum |
| 100 grams | lanolin |
| 150 grams | talc |
| 210 grams | Cod-liver oil |
| 1000 grams | |

Salve Formulation 2

500 grams Indomethacin (50%)
500 grams Desitin ® brand ointment

Salve Formulation No. 3

10 grams Tryptophan (1%)
900 grams Desitin ® brand ointment.

The active ingredient may include 1-(4-chlorobenzoyl)-5-methoxy-2-methyl-1H-indole-3-acetic acid, alternatively referred to as, 1-(p-chlorobenzoyl)-5-methoxy-2-methylindole-3-acetic acid commonly referred to as Indomethacin, alternatively the active ingredient may include other Indole based compound, such as Indole-3-ethanol (Tryptophol)
Indole-2-carboxylic acid
Indole-3-propionic acid
Indole-3-acetic acid
L-alpha-amino-3-indole propionic acid, which is also commonly referred to as L-Tryptophan The active ingredient, for instance Indomethacin, may be used in the Desitin ® or the 40% Zinc Oxide base described in salve formulation No. 1, above, in a concentration from 0.1% active ingrendient to concentrations approaching the pure active ingredient.

In all formulations the ingredients are mixed thoroughly to assure uniform distribution of the primary active ingredient through the base. The percentage concentration of the primary ingredient is listed adjacent to the ingredient. Since suggested courses of treatment will require concentrations less than those listed above, the concentrations of the primary active ingredient may be reduced simply by reducing the proportionate amount used in the preparation of the salve. For instance, in Salve No. 1 Indomethacin has a concentration of 3%. This concentration can be reduced to 1% simply by reducing the weight of Indomethacin from 30 grams to 10 grams and simultaneously increasing the weight of petrolatum from 820 to 840 grams.

Physicians and other professionals may, at the risk of some side effects which may include local skin irritation, apply the pure Indole or Indole derivatives, powder or liquid, directly to the lesion.

Solution Formulation No. 1

10 grams Indomethacin (1%)
745 grams ethanol
245 grams water

A 0.1% solution is formed by adding only 1 gram Indomethacin to the adjusted weights of water and ethanol.

In all formulations employing the granular form of the active agent the ingredients must be mixed thoroughly to assure distribution of the active agent throughout the preparation.

TREATMENT

Facial Herpes

In the following instruction Indomethacin is used. However, Indomethacin is intended to be a reference drug only for these examples. Other compounds containing indole can be substituted for Indomethacin, with various degrees of effectiveness.

Clean the lesion or sensitive area with a 1% solution of Indomethacin solution, dry, and apply three percent Indomethacin salve No. 1. Repeat the process every 4-6 hours until healing is observed. Then continue with 1% Indomethacin salve until healing is substantially complete. Then apply the salve with 0.1% concentration every 12 hours for three days to prevent recurrance.

Genital Herpes

Clean the lesion or sensitive area with 1% Indomethacin solution, dry and apply the three percent salve No. 1. Repeat every four hours or as needed until itching is suppressed by the salve, and does not recurr.

Continue treatments with a 1% Indomethacin salve No. 1. After healing is substantially complete, continue with 0.1% salve twice a day for four days to prevent recurrance. Lightly applied, regularly changed dressings may be used to protect clothing.

While the salves, and process of this application do effectively prevent and treat the external symptoms of Herpes infection, in no sense is it claimed that the treatments set forth a cure for the patient of the underlying disease, though in some cases they may. In fact, recurrence in the same or other location is possible or likely under those stimuli which might cause any dormant Herpes virus in the body to become active.

Having described this invention, it will be clear that many changes and modifications can be made thereto without altering the spirit or the scope thereof, and that all such changes are contemplated as falling within the scope of the following claims.

I claim:

1. A salve formation for topical treatment of inflammations and lesions of the human skin due to Herpes type virus which includes as the active ingredient Indomethacin in a concentration of over 0.1% by weight and said active ingredient is suspended in a carrier comprising:
Zinc Oxide in a concentration of 40% by weight,
petrolatum,
lanolin,
talc, and
Cod-liver oil.

2. The formulation of claim 1, wherein said active ingredient comprising a concentration of 0.1% to 3% by weight of said salve formulation.

3. A salve formulation for topical treatment of inflammations and lesions of the human skin due to Herpes type virus which includes Indomethacin in a concentration of 0.1% to 3% by weight as the active ingredient which is suspended in a carrier comprising:
Zinc oxide in a concentration of 40% by weight,
petrolatum in a concentration of 14% by weight,
lanolin in a concentration of 10% by weight,
talc in a concentration of 12% by weight, and
Cod-liver oil in a concentration of 21% by weight.

4. The formulation of claim 3 wherein said carrier is Desitin ® brand ointment.

5. A method for topical treatment of inflammations and lesions of the human skin due to Herpes type virus which includes the steps of applying to the surface of the skin the salve formulation recited in claim 1.

6. A method for topical treatment of inflammations and lesions of the human skin due to Herpes type virus which includes the steps of applying to the surface of the skin the salve formulation recited in claim 3.

7. A method for topical treatment of inflammations and lesions of the human skin due to Herpes type virus which includes the steps of applying to the surface of the skin the salve formulation recited in claim 4.

* * * * *

UNITED STATES PATENT AND TRADEMARK OFFICE
CERTIFICATE OF CORRECTION

PATENT NO. : 4,672,074

DATED : June 9, 1987

INVENTOR(S) : Alfred J. Harendza-Harinxma

It is certified that error appears in the above-identified patent and that said Letters Patent are hereby corrected as shown below:

On title page, under U.S. PATENT DOCUMENTS, at 4,309,414 correct "Iragi" to --Inagi--.

On col. 1, at line 35 correct "Indole-3-carboxylic acid" to --Indole-2-carboxylic acid--;

On col. 3, at line 19 correct "more areas" to --more hours--; and at lines 64-65 correct "aterioles" to --arterioles--;

On col. 4, at line 38 correct "Mononuleosis" to --Mononucleosis--; and

On col. 5, line 6 correct "acetylsalicyclic" to --acetylsalicylic--; and at line 60 correct "900" to --990--.

Signed and Sealed this

Ninth Day of February, 1988

*Attest:*

DONALD J. QUIGG

*Attesting Officer*　　　　*Commissioner of Patents and Trademarks*